(12) United States Patent
McCormick

(10) Patent No.: US 9,835,529 B2
(45) Date of Patent: Dec. 5, 2017

(54) BIOLOGICAL SPECIMEN HANDLING APPARATUS AND METHOD

(71) Applicant: SAKURA FINETEK U.S.A., INC., Torrance, CA (US)

(72) Inventor: James B. McCormick, Lincolnwood, IL (US)

(73) Assignee: SAKURA FINETEK U.S.A., INC., Torrance, CA (US)

( * ) Notice: Subject to any disclaimer, the term of this patent is extended or adjusted under 35 U.S.C. 154(b) by 0 days.

(21) Appl. No.: 14/189,894

(22) Filed: Feb. 25, 2014

(65) Prior Publication Data

US 2014/0273079 A1    Sep. 18, 2014

Related U.S. Application Data

(60) Provisional application No. 61/794,699, filed on Mar. 15, 2013.

(51) Int. Cl.
*G01N 1/36* (2006.01)

(52) U.S. Cl.
CPC ........................................ *G01N 1/36* (2013.01)

(58) Field of Classification Search
CPC ......................................................... G01N 1/36
See application file for complete search history.

(56) References Cited

U.S. PATENT DOCUMENTS 3,218,896 A * 11/1965 McCormick ............. G01N 1/06
                                                            269/7
4,623,308 A * 11/1986 Hellon ........................... 425/117
5,080,869 A * 1/1992 McCormick .................. 422/547
5,284,753 A * 2/1994 Goodwin, Jr. ................... 435/30
6,284,113 B1 * 9/2001 Bjornson ............. B01J 19/0046
                                                            204/450

(Continued)

FOREIGN PATENT DOCUMENTS

EP          0142575       5/1985
JP        2005351822     12/2005

(Continued)

OTHER PUBLICATIONS

Sakura Finetek, PCT Search Report/Written Opinion dated Jun. 4, 2014 for PCT App No. PCT/US2014/022003.

(Continued)

*Primary Examiner* — Jyoti Nagpaul
(74) *Attorney, Agent, or Firm* — Blakely Sokoloff Taylor & Zafman; Tom Babbitt

(57) ABSTRACT

In accordance with one aspect of the invention, a mold is provided for receiving a tissue specimen and molten embedding material that improves the ease of withdrawing the embedded tissue specimen. The mold has a barrier coating intimately bonded to one or more surfaces of the mold that repels the attraction of the embedding material to the one or more mold surfaces and produces a positive meniscus of the embedding material in the mold. The barrier coating permits the mold to be re-used without needing to manually re-apply a release agent to the mold before using the mold. Further, the barrier coating permits the use of more aggressive draft angles than conventional molds by reducing the frictional engagement between the embedding material and the mold cavity surfaces.

7 Claims, 12 Drawing Sheets

(56) References Cited

U.S. PATENT DOCUMENTS 7,234,308 B1 * 6/2007 Critz ................ A01N 1/02
249/111

FOREIGN PATENT DOCUMENTS

| JP | 2009507231 | 2/2009 |
|---|---|---|
| WO | WO-2006089365 | 2/2006 |
| WO | WO-2007028202 | 3/2007 |

OTHER PUBLICATIONS

Sakura Finetek U.S.A., Inc., "International Preliminary Report on Patentability", International Appln. No. PCT/US2014/022003, (dated Sep. 24, 2015).
Sakura Finetek U.S.A., Inc., "Patent Examination Report No. 1", AU Application No. 2014237575, (dated Apr. 22, 2016).
Sakura Finetek U.S.A., Inc., "Non-Final Office Action", JP Application No. 2015-561731, (dated Jul. 25, 2016).
Sakura Finetek U.S.A., Inc., "Examiner's Report", CA Application No. 2,901,423, (dated Sep. 28, 2016).
Sakura Finetek U.S.A., Inc., "Patent Examination Report No. 2", AU Application No. 2014237575, (dated Sep. 28, 2016).

* cited by examiner

BIOLOGICAL SPECIMEN HANDLING APPARATUS AND METHOD

CROSS-REFERENCE TO RELATED APPLICATION

The application claims the benefit of the earlier filing date of U.S. Provisional Patent Application No. 61/794,699, filed Mar. 15, 2013 and incorporated herein by reference.

FIELD

The invention relates to embedding tissues for histological examination and, more particularly, relates to improved apparatus and methods for embedding tissue specimens in wax or the like in preparation for microtome sectioning and microscopic examination.

BACKGROUND

Standard procedures for preparing tissue specimens for microscopic examination involve multiple processes that end with the specimen infiltrated with paraffin, embedding the tissue specimen in paraffin wax, and sectioning the paraffin-embedded tissue specimen very thinly with a microtome. Typically, prior to embedding, the tissue specimen is treated by fixing, dehydrating, clearing, and saturating the tissue specimen with various fluids, including formaldehyde and water, ethanol, xylene.

Initially, a molten embedding material, such as a paraffin wax compound, is poured into a cavity of a mold to partially fill the mold cavity. The mold is moved to a cooling station where a bottom wall of the mold cavity is placed on a cooling rail to solidify or gel the paraffin in mold cavity. Next, the prepared tissue specimen is placed onto the gelled paraffin in the cavity of the mold. Positioning the tissue specimen onto the gelled paraffin involves orienting the tissue specimen to best present the specimen to the cutting blade of a microtome instrument. The tissue specimen is oriented such that consecutive cross sections produced from the tissue specimen show features of the tissue specimen throughout the tissue specimen. For example, a relatively long and thin tissue specimen may be oriented to extend substantially normal to a bottom wall of the mold cavity so that a healthcare provider can view the sequential cross sections and understand the features of the tissue specimen along its length.

Molten paraffin is then poured over the tissue specimen. A cassette or capsule having paraffin thereon is placed over the cavity in the mold and additional molten paraffin is poured over the cassette. After the paraffin solidifies, a cast block is formed that includes a base portion of the cassette or capsule and a paraffin block portion having the tissue specimen disposed within the block portion. In accordance with standard procedure, the size of various cassettes and capsules have been developed for processing tissue specimens, and have become relatively standardized so that the base portions of the cassettes and capsules are the specimen carriers to be placed within a chuck in a microtome sectioning device.

A common problem with using paraffin wax to embed a tissue specimen within a mold is that the wax sticks to the inner mold surfaces after cooling and resists removal of the embedded specimen casting from the mold. One solution to this problem is to treat the mold with a release solution, such as a soap-like solution, by spraying the mold with the release agent before pouring the paraffin into the mold. As will be appreciated, preparing a number of tissue specimens involves spraying each mold with the release solution which complicates and slows the process of preparing the tissue specimens. The complication caused by spraying each mold is especially acute in the context of production needs for efficiency when dozens or hundreds of embedded tissue specimens are required to be prepared. Further, with reusable molds, the release solution is typically applied each time the mold is used. The continual use of release solution increases the cost and difficulty of preparing tissue specimens and adversely affects the financial and environmental benefits of utilizing reusable molds.

SUMMARY

In accordance with one aspect of the invention, a mold is provided for receiving a tissue specimen and molten embedding material that solidifies in the mold with the tissue specimen embedded therein with the mold configured to facilitate the withdrawal of solidified material including the embedded tissue specimen from the mold.

In another aspect, a mold for receiving a tissue specimen and molten embedding material is provided which is configured to modify a configuration of the solidified embedding material compared to solidified embedding material produced using conventional molds. Sectioning solidified embedding material produced using conventional molds results in edges of the sectioned embedding material that interfere with impact welding of the sections as they fall from a microtome machine which has performed the sectioning. To address this problem, a mold is described that has cavity sidewalls with a draft angle in the range of approximately zero to approximately two degrees which are more aggressive than conventional molds. The mold produces a block portion of the hardened embedding material (with tissue specimen therein) with a more uniform cross section along the depth of the mold cavity. The more uniform cross section of the hardened embedding material block portion produces more square outer edges of sections of the block portion once the block portion has been sectioned using a microtome instrument. The more square edges are advantageous because such edges permit higher-strength impact welds between sections of the block portion as they fall from the microtome instrument and thereby improve ribboning of the block portion sections.

In another aspect, the mold also reduces adhesion of the embedding material to the interior surfaces of the mold. This reduction in adhesion produces a smaller crystalline structure of the hardened embedding material so that the outer surfaces have a smooth, glass like texture and are more translucent than outer surfaces of hardened embedding material produced using traditional molds. Further, the increased translucency of outer surfaces of the hardened embedding material permit features of an embedded object, such as a tissue sample, to be more clearly visually observed than an embedded object within hardened embedding material produced using a conventional mold. This is of benefit in visually determining the completeness of the embedding material infiltration into the tissue sample as well as visually determining the tissue specimen size and shape that will be presented to the cutting edge of the microtome instrument.

In one embodiment, a mold has a barrier coating intimately and permanently bonded to one or more surfaces of the mold that repels the attraction of the embedding material to the one or more mold surfaces. The permanently bonded barrier coating thereby permits the mold to be re-used without, for example, needing to manually re-apply a release agent to the mold before re-using the mold. This simplifies the process of re-using the mold and eliminates the cost and complication of having to spray each mold before use with a release agent.

In one form, the barrier coating has oleophobic and hydrophobic properties that resist the capillary forces or action that would otherwise be present between the embedding material and the metallic material of the uncoated mold. The barrier coating may be a nano-layer material that is molecularly bonded to one or more surfaces of the mold. The barrier coating is particularly well suited for improving the use of paraffin wax as an embedding material, which exhibits an affinity to many different types of materials commonly used to manufacture molds. Further, the barrier coating resists adhesion of the embedding material to the mold, which reduces the imperfections in the outer surfaces of the hardened embedding material. Because of the reduction in imperfections, the outer surfaces of the hardened embedding material have a smooth, glass-like texture and are more translucent than the outer surfaces of hardened embedding material produced using conventional molds. This is of benefit in visually determining the completeness of the embedding material infiltration into the tissue sample as well as visually determining the tissue specimen size and shape that will be presented to the cutting edge of the microtome instrument.

The mold may have a cavity with a bottom wall, sidewalls, and the barrier coating intimately bonded to interior surfaces of the bottom wall and the sidewalls. The sidewalls of the mold are oriented at an angle relative to the bottom wall, sometimes referred to as a draft angle, to make it easier to remove the embedded tissue specimen once the embedding material has hardened. Conventionally, a higher draft angle (e.g., five degrees) was used to ensure proper release of the embedding material after it has hardened and shrunk. However, the barrier coating of the instant application permits the use of more aggressive draft angles (e.g., approximately zero, one, and two degrees) than conventional molds by reducing the coefficient of friction between the embedding material and the mold cavity surfaces which minimizes the sticking of embedding material to the mold cavity surfaces. The reduced coefficient of friction makes the process of removing the hardened embedding material and tissue specimen therein less dependent on the draft angle and permits mold shapes to be used that are impractical with conventional molds that require a draft angle for the mold sidewalls.

More aggressive draft angles are beneficial in some applications because the hardened block of embedding material can have a cross section along the mold sidewalls with a margin angle formed by the mold drat angle that is closer to zero degrees than conventions molds, which typically produce cross section margin angles of several degrees. The zero degree cross section margin angle of the hardened block of embedding material produces sections of the hardened block that have a near zero degree cross section margin angle from one section to the next as the block passes through a microtome. Stated differently, a conventional, less aggressive mold sidewall draft angle can produce a more pyramidal shape of the hardened embedding material (and tissue specimen therein) with a larger cross section near the cassette and a smaller cross section near the bottom wall of the mold cavity. By contrast, a block of hardened embedding material according to an embodiment described herein can have a more box-like shape with a cross-section that is substantially the same near the cassette as near the bottom wall of the mold cavity. This more uniform cross section may make subsequent handling of consecutive sections of cut tissue specimens easier and more accurate, which is especially beneficial and will assist consecutive sections to adhere to each other and form a ribbon. The ribbon effect is important in some approaches for preparing consecutive serial sections that are a routine requirement and best practice.

In accordance with another aspect, a method is provided for more efficiently preparing embedded tissue specimens for histological examination. The method includes providing a mold having a barrier coating bonded thereto, pouring a molten embedding material into the mold and into contact with the barrier coating, and positioning a tissue specimen in the embedding material. Additional molten embedding material is then poured over the tissue specimen to fill a cavity of the mold. The barrier coating has an oleophobic property that resist the capillary forces present in the embedding material. Because the coating resists the capillary forces of the embedding material poured into the mold, the capillary forces are redirected back into the embedding material which raises a meniscus of the embedding material which has been poured over the tissue in the mold. Stated differently, the resistance of the barrier coating to the capillary forces of the embedding material produces a positive meniscus that is generally convex and can crown outwardly above the mold cavity. By contrast, paraffin poured into a conventional mold has a negative meniscus that bows downwardly into the mold cavity.

Next, a cassette warmed to a temperature at or above the melting point of the embedding material is introduced into the mold and into contact with the outwardly crowning meniscus of the embedding material. In most instances, the outwardly crowning meniscus provides sufficient volume to fill perforations in the cassette bottom and weld the cassette to the tissue specimen within the solidified embedding material after the cassette is introduced into the mold. This provides a significant increase in efficiency because an operator or machine performing the embedding may not need to subsequently pour additional embedding material over the cassette in order to weld the tissue sample to the cassette. Another advantage of the outwardly crowning meniscus is that the fill level of the mold can more easily be visually determined by the technician than with conventional molds whose sidewalls visually obscure the inwardly bowing, negative meniscus thereof.

In an alternative approach, a one-pour fill procedure can be used to fill the mold cavity rather than partially filling the cavity with embedding material and placing the tissue sample on the embedding material. Specifically, molten embedding material is poured into the mold until the positive meniscus of the embedding material crowns outwardly from the mold cavity. Next, the bottom wall of the mold cavity is cooled (such as by using a cooling rail) to begin to solidify the embedding material near the cavity bottom wall. The tissue specimen can be advanced into the upwardly crowning meniscus, through the still molten embedding material thereat, and positioned upon the hardened embedding material near the cavity bottom wall. Thus, a single pour of embedding material may be sufficient to fill the cavity and provide enough embedding material to weld the cassette to the embedding material.

The method further includes solidifying or hardening the embedding material about the tissue specimen and its mated cassette. The solidified or hardened embedding material welded to the cassette and the embedded tissue specimen in the mold are then removed as one from the embedding mold. Some embedding materials, such as paraffin wax, are sticky or tacky when molten and become less sticky as they cool and harden. The barrier coating of the mold, as described herein, inhibits frictional engagement of the embedding material to the surfaces of the mold from the moment the embedding material is poured into the mold. The oleophobic mold coating resists the sticky embedding material and thereby reduces the coefficient of friction between the embedding material and the mold cavity when the embedding material is molten, partially hardened, and fully hardened. Because there is less frictional engagement between the embedding material and the mold, a user can withdraw the cassette welded in bond to the embedded tissue specimen from the mold before the embedding material has fully crystallized and hardened. This provides a significant improvement in efficiency since the user does not have to wait for the embedding material to fully crystallize before withdrawing the cassette and associated embedded tissue specimen from the mold. For example, it has been discovered that this method reduces the time involved in preparing an embedded tissue specimen by approximately five percent to approximately twenty-five percent over traditional approaches. This improvement expedites the process of achieving an early diagnosis of the tissue sample and can expedite treatment of a patient. The improved efficiency is also advantageous in the context of automated machines for producing embedded tissue specimens, where reducing the time spent hardening the embedding material can increase the throughput of the machine.

DETAILED DESCRIPTION OF THE PREFERRED EMBODIMENTS

Figure 1:
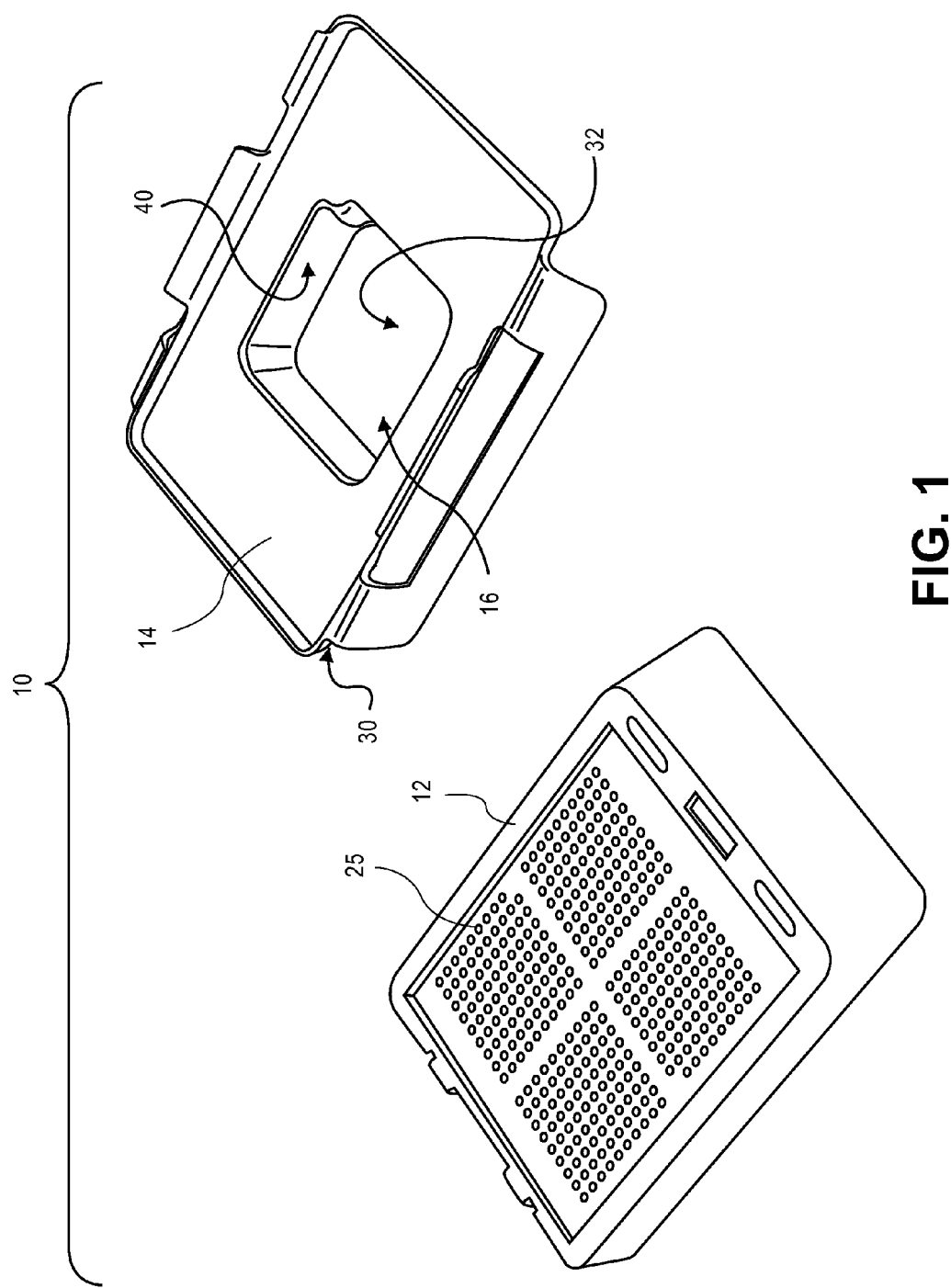
FIG. 1 is a top, perspective view of a cassette and embedding mold for use with the cassette.

With reference to FIG. 1, a tissue specimen handling device 10 is disclosed having a cassette 12 and a mold 14 configured to receive the cassette 12. The mold 14 has a cavity 16 into which a molten embedding material, such as paraffin wax 20, is introduced (e.g., poured) and a tissue specimen 22 is inserted (see FIG. 2B). The cavity 16 has sidewalls 30 and a bottom wall 32 with a barrier coating, such as coating 40, bonded thereto that repels the attraction of the paraffin wax 20 to the sidewalls 30 and bottom wall 32. With reference to the schematic illustration of FIG. 2B, the mold 14 has an interior portion 42 and an exterior portion 44, with the coating 40 being intimately bonded with the material of the mold 14 at the interior portion 42. Because the coating 40 is intimately bonded to the mold interior portion 42, the mold 14 can be used to prepare an embedded tissue specimen without the need to spray a release agent onto the mold 14 before each use (as was done in some prior approaches). In one form, the coating 40 is bonded to both the interior and exterior portions 42, 44 of the mold 14 through a process that involves spraying the mold 14 with the coating 40 or dipping the mold 14 in the coating 40.

The coating 40 reduces the coefficient of friction between the paraffin 20 and the cavity 16 and permits the cassette 12 and embedded tissue specimen 22 to be withdrawn from the cavity 16 before the paraffin 20 has completely hardened, which reduces downtime during production of the embedded tissue specimen 22. Further, because the coefficient of friction is reduced, the coating 40 reduces reliance on the use of large draft angles to achieve release of the hardened paraffin 20 from the mold 14. The coating 40 therefore permits the use of more aggressive draft angles and a greater variety of mold shapes.

Figure 2A:
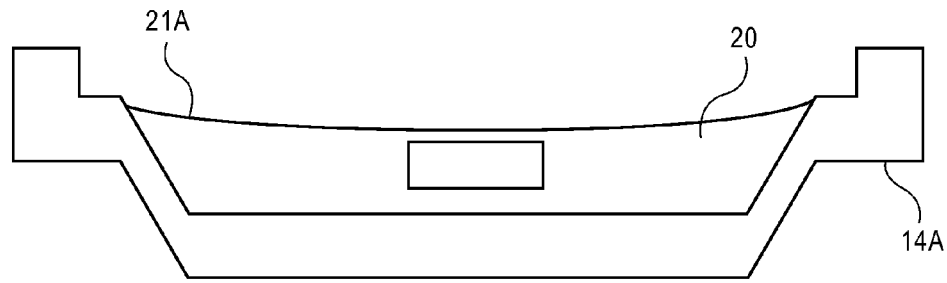
FIG. 2A is a schematic side view of a traditional mold with a tissue specimen disposed in paraffin wax within the mold and an inwardly bowing, negative meniscus of the paraffin wax.
Figure 2B:
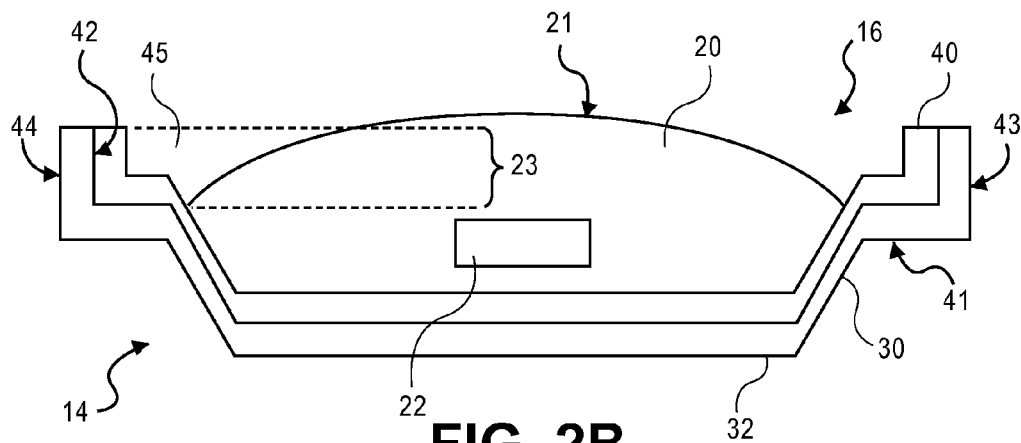
FIG. 2B is a schematic side view of a mold having an inner portion with a barrier coating bonded thereto, a tissue specimen disposed in embedding material within the mold, and an outwardly crowning, positive meniscus of the embedding material.

The coating 40 is configured to resist the capillary action of the paraffin 20 once the paraffin 20 has been poured into the mold 14, as shown in FIG. 2B. The capillary forces are redirected back into the paraffin 20 which raises a meniscus 21 of the paraffin 20 which has been poured over the tissue specimen 22 in the mold 14. The meniscus 21 crowns outwardly from the mold cavity 16 and has a generally convex appearance, as shown in FIG. 2B. By contrast, a traditional mold 14A (see FIG. 2A) without the barrier coating 40 produces an inwardly bowed, negative meniscus of paraffin 20 because the capillary forces between the paraffin 20 and the surfaces of the mold 14 draw the paraffin 20 upward along the interior surfaces of the mold 14.

Figure 2D:
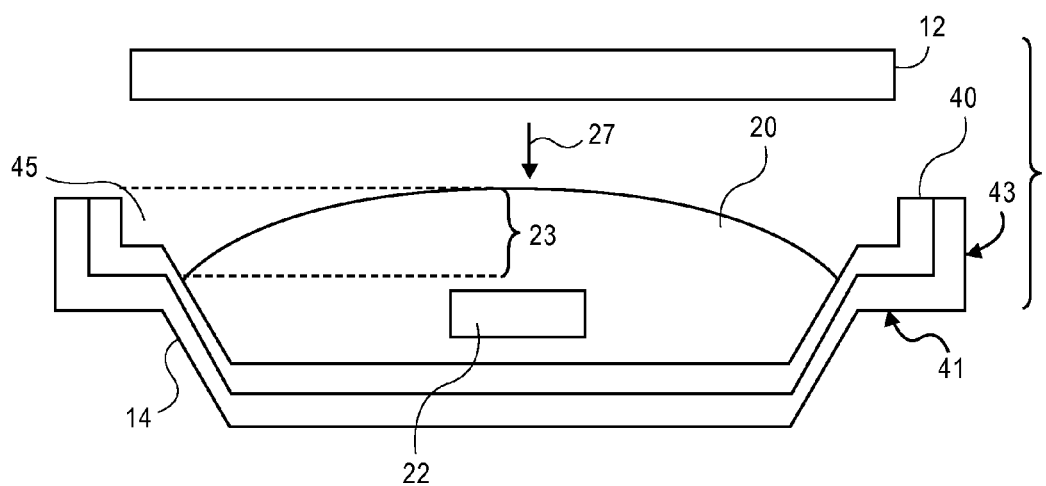
FIG. 2D is a schematic side view of the mold of FIG. 2B showing a cassette being introduced into the mold.
Figure 2C:
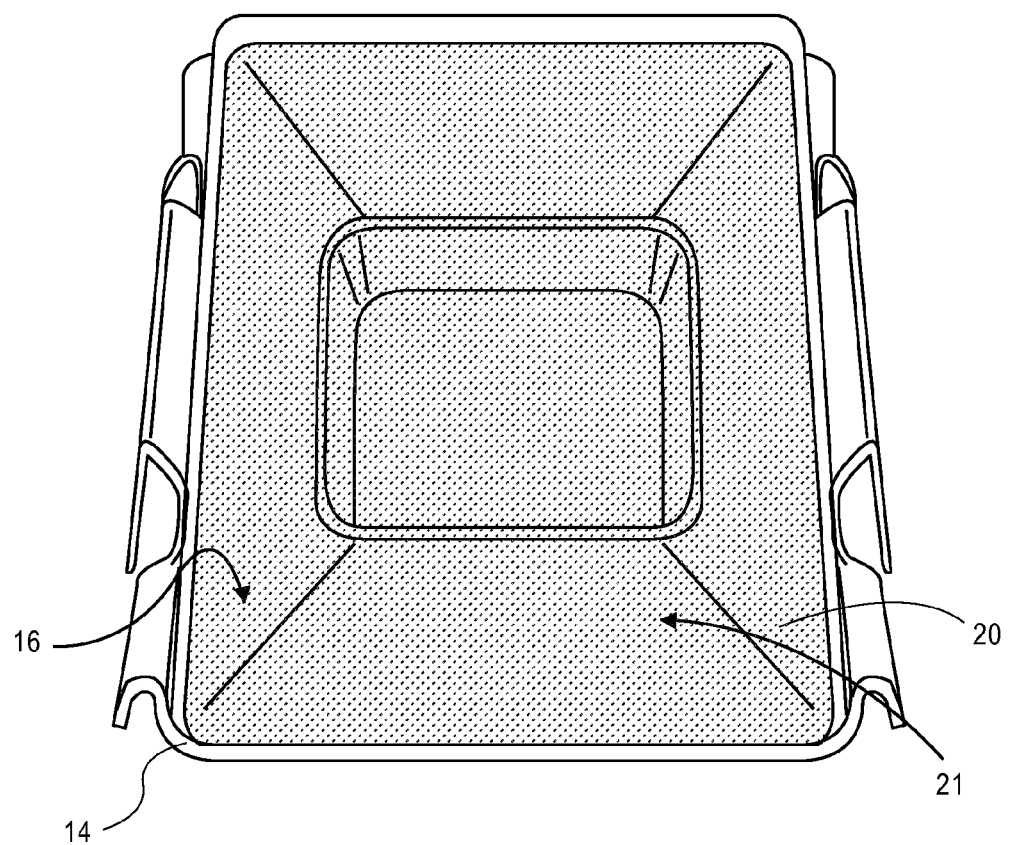
FIG. 2C is a top, perspective view of a mold having a barrier coating similar to the mold of FIG. 2B and shows an outwardly crowning meniscus of the embedding material.
Figure 2E:
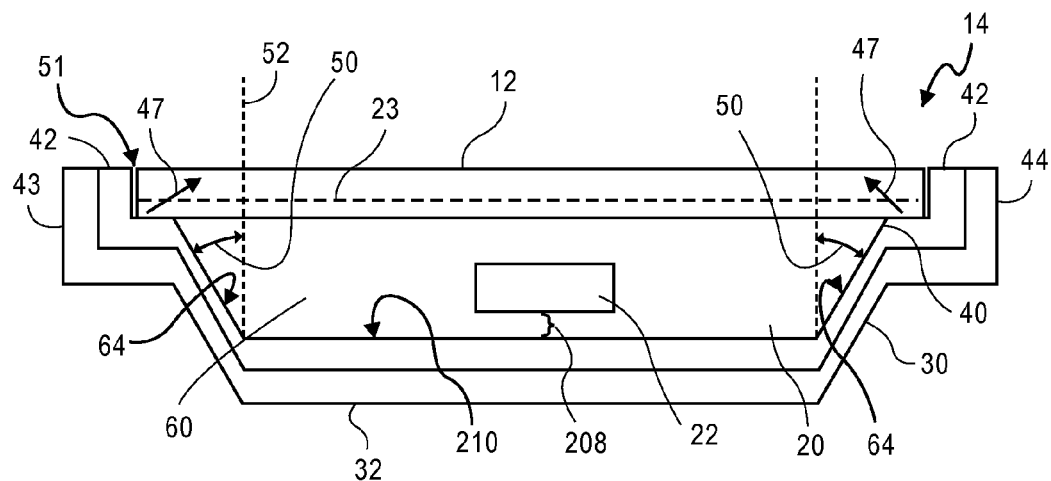
FIG. 2E is a schematic side view of the mold of FIG. 2B showing the cassette contacting the embedding material.

The outwardly crowning meniscus 21 produces a raised portion 23 of the paraffin 20 (raised, in one embodiment, above mold cavity 16). The outwardly crowning meniscus 21 with raised portion 23 of paraffin 20 is positioned to contact and fill perforations 25 in the cassette 12 (see FIG. 1) as the cassette 12 is introduced in direction 27 into the mold 14, as shown in FIGS. 2D and 2E. Thus, by pouring paraffin 20 into the mold 14 to raise the outwardly crowned meniscus portion 23 to a predetermined height within the mold 14, the cassette 12 can be introduced into the mold 14 and welded to the hardening paraffin 20 without the need to pour additional paraffin 20 over the cassette 12. This provides an increase in efficiency of preparing embedding tissue samples because the user or machine performing the process can secure the cassette 12 to the paraffin 20 with fewer pours of paraffin 20.

Another advantage of the mold 14 is that it provides improved take-up of the paraffin 20 into the cassette 12 when the cassette 12 is lowered into the mold 14. More specifically, the mold 14 has an upper tray portion 41 and outer walls 43 upstanding from the upper tray portion 41 that form an upper cavity 45 sized to receive the cassette 12, as shown in FIGS. 2B and 2D. The upper tray portion 41 and outer walls 43 include the interior portion 42 having the barrier coating 40 bonded thereto. Because the barrier coating 40 resists the capillary forces from the paraffin 20, the outer walls 43 produce a repelling force on the paraffin 20 in a direction toward the center of the upper cavity 45 and the upper tray portion 41 produces a repelling force on the paraffin 20 in an upward direction out of the mold 14. These repelling forces combine to drive the paraffin 20 generally in direction 47 toward the center of the cassette 12, as shown in FIG. 2E. This improves take-up of the paraffin 20 by directing the paraffin 20 toward the perforations 25 in the center of the cassette 12 and away from the area between the mold upstanding outer walls 43 and the unperforated sidewall sections 49 of the cassette 12 (see FIG. 1).

The mold 14 also provides improved resistance to spill-over of the paraffin 20 when the cassette 12 is introduced into the mold 14. With reference to FIGS. 2D and 2E, inserting the cassette 12 by lowering it into the mold 14 increases the hydraulic pressure on the paraffin 20. The paraffin 20 tends to take a path of least resistance in response to the increase in hydraulic pressure. For example, the paraffin 20 may flow toward the areas of the cassette 12 and mold 14 where the capillary forces between the paraffin 20 and the cassette 12 or mold 14 are the greatest. Thus, the relatively small perforations 25 of the cassette 12 and material of the cassette 12 produce capillary forces with the paraffin 20 that draws the paraffin 20 upward into the cassette perforations 25.

The increase in hydraulic pressure caused by lowering the cassette 12 into the mold 14 also tends to direct paraffin 20 near the outer walls 43 upward into a gap 51 (see FIG. 2E) between the cassette 12 and the outer walls 43. In conventional molds such as mold 14A, this hydraulic pressure drives the paraffin 20 upward through the gap 51 and causes the paraffin 20 to spill over from the sides of the mold 14A if there is sufficient paraffin 20 present in the mold 14. An increase in hydraulic pressure in the paraffin 20 caused by lowering the cassette 12 into the mold 14, in combination with the capillary forces between the cassette 12, mold 14, and paraffin 20 in the gap 51, draws the paraffin 20 upward into the gap 51 in the conventional mold 14A and causes the paraffin 20 to spill over from the sides of the mold 14A.

However, the mold 14 as described herein having outer walls 43 and barrier coating 40 possess oleophobic and/or hydrophobic properties that apply a repelling force on the paraffin 20 toward the center of the upper cavity 45, as discussed above. This action resists flow of the paraffin 20 into and along the gap 51 and instead directs the flow inwardly toward the cassette perforations 25. Further, the barrier coating 40 reduces the capillary forces produced between the mold 14 and the paraffin 20 within the gap 51. This increases the resistance to the paraffin 20 traveling upward through the gap 51 (by lowering the capillary forces) and spilling outward from the mold 14 upon lowering the cassette 12 into the mold 14 such that the paraffin 20 is instead drawn into the perforations 25 of the cassette 12. Thus, the mold 14 resists spill-over of paraffin 20 when the cassette 12 is introduced into the mold 14 and improves the ease of use of the mold 14.

Yet another advantage of the outwardly crowning or positive meniscus 21 is that it improves the ease and accuracy of visually judging when the mold 14 has been sufficiently filled with paraffin 20. This is in contrast to the conventional molds 14A, where the mold walls may visually obscure the inwardly bowing meniscus of the paraffin 20.

The mold 14 is preferably made of a polished stainless steel material, although other materials may be used, such as one or more metals, alloys, ceramics, and plastics. The coating 40 is permanently bonded to the mold 14, has oleophobic and/or hydrophobic properties, and retains its paraffin-resisting properties through many uses of the mold 14. The coating 40 has a surface energy that resists capillary forces in the paraffin 20, re-directs the capillary forces back into the paraffin 20, and inhibits the paraffin 20 from bonding with the material of the mold 14. The surface energy of the coating 40 is achieved by the application of a nano-scale molecule that makes a permanent molecular bond to the mold 14.

The coating 40 may be produced with a number of different formulations including different compositions and nano-particle sizes. The coating 40 may include fused glaze (e.g., silica/glass), organic fused and liquid fluorocarbons (i.e., silicone and Teflon), and oleophobic materials that possess a surface energy which rejects a variety of molecules of animal, vegetable, organic chemical and petrochemical hydrocarbon materials.

The coating 40 may be applied to the mold 14 by spraying one or more surfaces of the mold 14 with the coating 40. In another approach, the mold 14 is dipped in a container in which the liquid barrier coating 40 is disposed. When dipping is performed, the coating material is attracted by molecular bonding to the mold 14 and excess coating material, i.e., material which has not bonded to the mold 14, falls off of the mold 14 as it is withdrawn from the coating material. The entire mold 14 can be submerged in the liquid coating material so that all surfaces thereof are covered with the coating material.

In one form, the coating 40 is a nano-scale treatment provided by Aculon, Inc. The nano-scale treatment utilizes highly ordered nano-scale films called self-assembled monolayers of phosphates (SAMPs). The coating 40 may include one or more components, such as a first material that provides the oleophobic and/or hydrophic properties and a second material that primes the mold 14 for bonding with the first material.

With reference to FIG. 2E, the tissue specimen handling device 10 is shown immediately after the tissue specimen 22 has been placed in the cavity 16, molten paraffin 20 poured over the tissue specimen 22, and the cassette 12 positioned in the mold 14.

Figure 3:
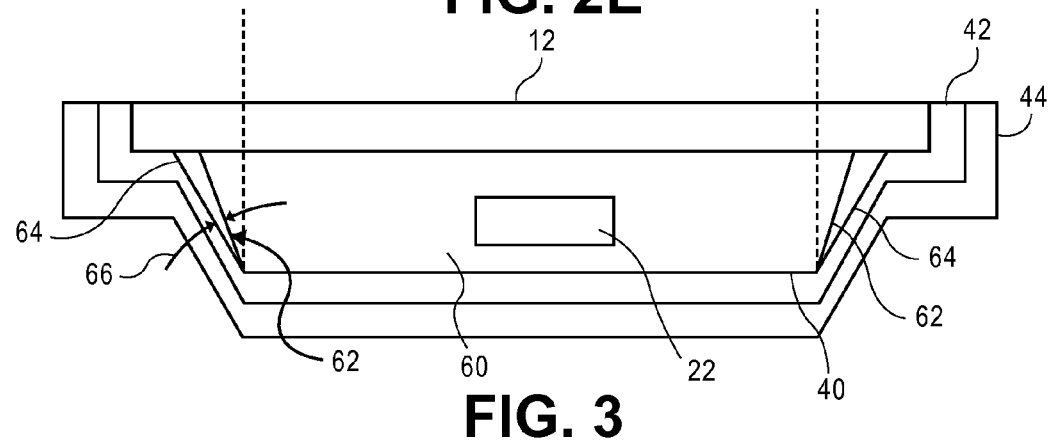
FIG. 3 is a schematic side view of the mold of FIG. 2B showing the embedding material having shrunk to be out of contact with sidewalls of the mold.

The mold cavity sidewalls 30 extend at a draft angle 50 relative to a perpendicular projection from a bottom wall of the cavity 16 (as illustrated, a vertical axis 52 of the cavity 16). As the paraffin 20 cools, it hardens into a generally block shaped portion 60 and the volume of the paraffin 20 decreases by about eight percent, as shown in FIG. 3. The decrease in volume of the paraffin 20 causes side surfaces 62 of the hardened wax block portion 60 to separate from inner surfaces 64 of the cavity sidewalls 30 to an orientation where there is a separation angle 66 between the wax block portion side surfaces 62 and the cavity sidewall inner surfaces 64, as shown in FIG. 3.

Figure 4:
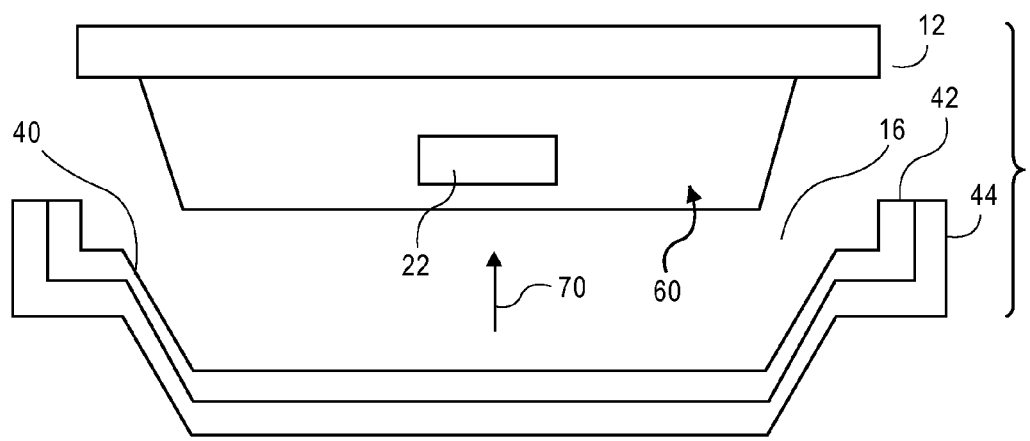
FIG. 4 is a schematic side view of the mold of FIG. 2B showing the cassette and embedded tissue specimen withdrawn from the mold.

The cassette 12 may then be lifted in direction 70 out of the mold 14 which draws the hardened wax block portion 60 and tissue specimen 22 embedded therein out of the cavity 16, as shown in FIG. 4. Because the coating 40 is intimately bonded to the interior portion 42 of the mold 14, the mold 14 may be re-used to prepare another embedded tissue specimen 22 without the need to apply a release agent, as in some prior approaches.

Figure 5:
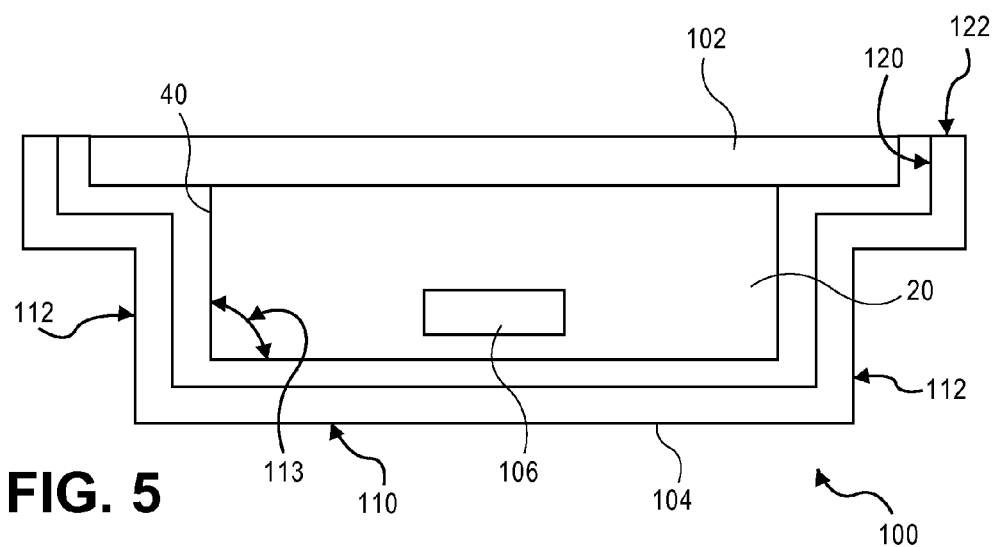
FIG. 5 is a schematic side view of another embodiment of a mold similar to the mold of FIG. 2B except that the mold of FIG. 5 has substantially vertical sidewalls.
Figure 6:
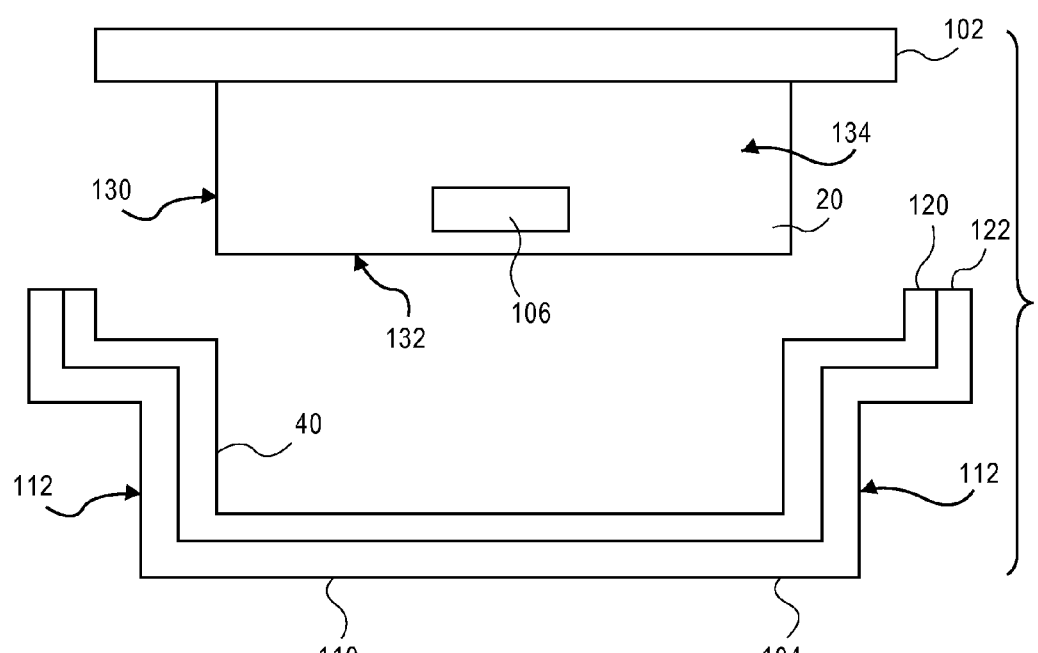
FIG. 6 is a schematic side view of the mold of FIG. 5 showing the cassette and embedded tissue specimen withdrawn from the mold before the embedding material has shrunk.

With reference to FIGS. 5 and 6, another tissue specimen handling device 100 is shown that is substantially similar to the tissue specimen handling device 10 discussed above. The device 100 includes a cassette 102 and a mold 104 for receiving a tissue specimen 106 and the paraffin wax 20. The mold 104 has a bottom wall 110 and sidewalls 112 upstanding from the bottom wall 110 at an included angle 113 relative to the bottom wall 110. The angle 113 may be in the range of, for example, approximately ninety to approximately ninety-two degrees. These orientations of the sidewalls 112 provide mold draft angles in the range of approximately zero to approximately two degrees, which are more aggressive than conventional designs. Like the mold 14, the mold 104 has an interior portion 120 with the coating 40 intimately bonded to the material of the mold 104. The mold 104 also has an exterior portion 122 opposite the interior portion 120, with the coating 40 being bonded to the exterior portion 122 in some approaches.

Figure 8:
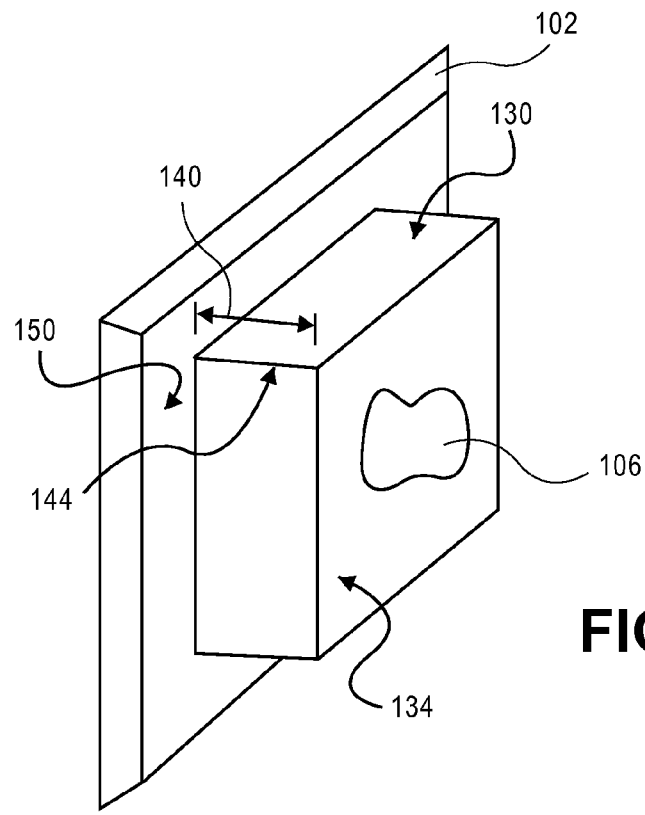
FIG. 8 is a top, perspective view of another embodiment of an embedded tissue specimen and cassette construct showing a generally box-shaped portion of the hardened embedding material.
Figure 7A:
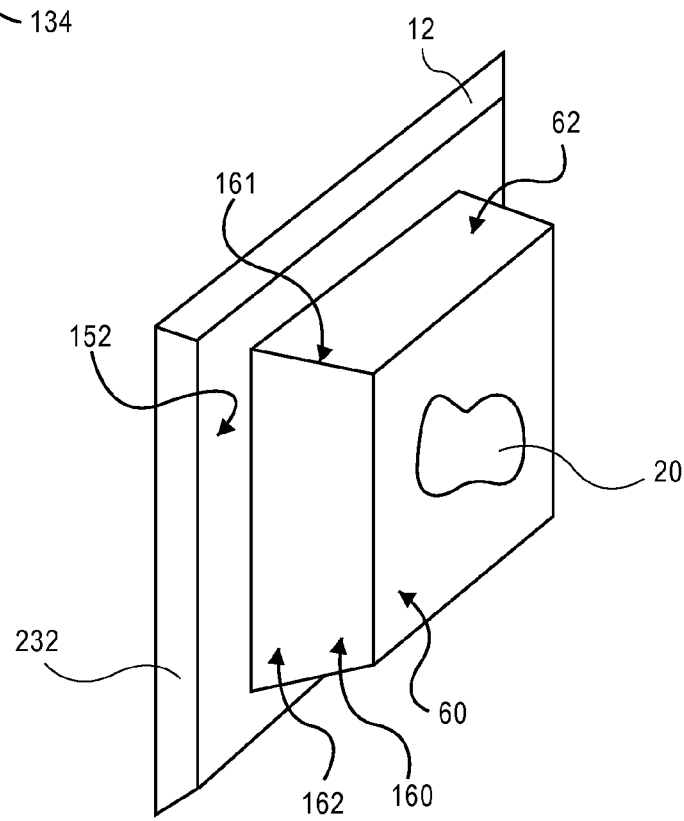
FIG. 7A is a top, side perspective view of an embedded tissue specimen and cassette construct showing a partially pyramidal-shaped portion of the hardened embedding material.
Figure 9:
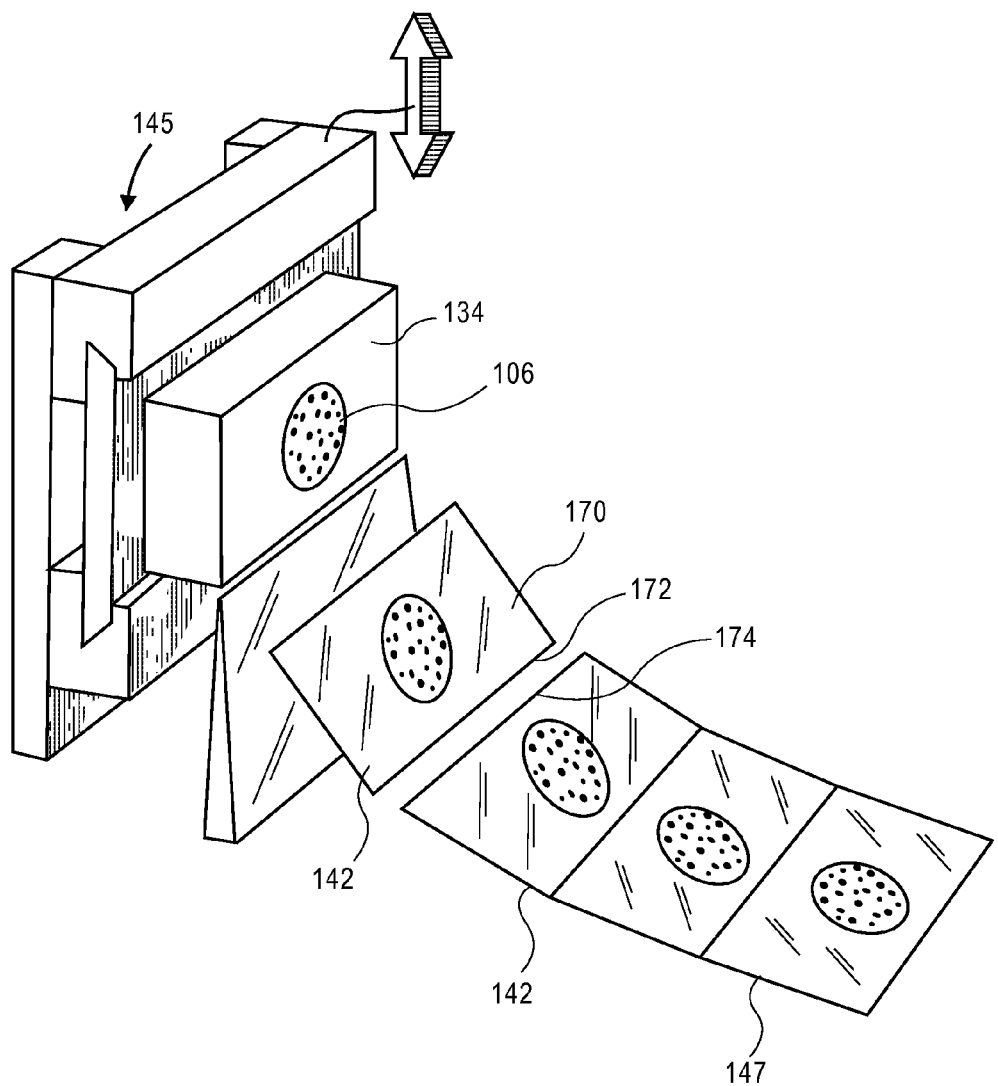
FIG. 9 is a side perspective view of the embedded tissue specimen and cassette construct of FIG. 8 clamped in a chuck and being cut by a microtome blade to form a ribbon of embedded tissue sections.

As shown in FIG. 6, the mold 104 has the sidewalls 112 oriented at a more aggressive draft angle than the sidewalls 30 of the mold 14, which has draft angles similar to conventional molds. The sidewalls 112 produce a more perpendicular orientation of side and bottom surfaces 130, 132 of a block shaped portion 134 of the hardened paraffin 20. This causes the block portion 134 to have a more box-like shape than the block portion 60 formed by mold 14 (and conventional molds having similar draft angles), as shown in FIGS. 7A and 8. The more aggressive draft angle of the mold 104, and the resulting cubic shape of the block portion 134, provides a more uniform cross section of the block portion 134 along a length 140 of the block portion 134 (or as measured along the mold sidewall 112). The more uniform cross section of block portion 134 produces more evenly sized embedded tissue specimen block sections 142 as the block portion 134 is cut by a microtome 145 into consecutive sections 142, as shown in FIG. 9. These more evenly sized embedded tissue specimen block sections 142 can be more easily handled than embedded tissue specimen portions produced from sectioning the paraffin block portion 60 produced by mold 14.

More specifically, the side surfaces 130 of the paraffin block portion 134 produced by mold 104 are generally orthogonal to a lower surface 150 of the cassette 102, whereas the side surfaces 62 of the paraffin block portion 60 produced by mold 104 are oriented more obliquely to its respective cassette lower surface 152, as shown in FIGS. 7A and 8. Thus, when the block portion 60 (or block portions of embedding material produced using a conventional mold) is sectioned, sections of the block cut from a leading end portion 160 will have a larger cross sectional area than sections of the block cut from a trailing end portion 162 (see FIG. 7A). By contrast, the embedded tissue specimen block sections 142 produced using the mold 104 will have a substantially uniform cross sectional area throughout the block portion 134, as shown in FIG. 9. The more uniform cross sectional area of the embedded tissue specimen block sections 142 permits automated machinery that handles the sections 142 to utilize tighter tolerances because the machinery needs to accommodate less variation in the sections 142. Thus, the combination of the coating 40 being intimately bonded with the interior portion 120 of the mold 104 and the use of more aggressive draft angles, which can be used because of the coating 40, improves the uniformity of sectioned embedded tissue specimen sections 142 and can improve tolerances throughout subsequent processing of the embedded tissue specimen sections.

Another advantage provided by the mold 104 is improved "ribboning" or impact adhesion of the sections 142 once the sections 142 have exited the microtome machine 145, as shown in FIG. 9. Stated differently, the mold 104 improves the ability of the sections 142 to stick to one another after sectioning. It has been found that the adhesion of one section 142 to the next is a function of the impact and surface geometries of the outer cut surface of one section 142 against the next section 142. The more perpendicular or square the relative orientation of side and bottom surfaces 130, 132 of the block portion 134, the greater the contact area and the more perfect the impact weld of mating flat surfaces 172, 174 of sections 142 after the sections 142 have exited the microtome machine 145 (see FIG. 9). This provides the optimum geometry for the surfaces 172, 174 to stick together and sections 142 to form a ribbon 147 after sectioning of the block portion 134.

An advantage shared by both of the molds 14, 104 is that corners 144, 161 of the paraffin block portions 60, 134 can be made with smaller radii of curvature than conventional molds (see FIGS. 7A and 8). Whereas conventional molds may use radii in the range of 5-10 mm for ease of release of the paraffin wax, the molds 14, 104 can utilize corners having radii in the range of about 2-3 mm because the barrier coating 40 makes the release of the hardened paraffin 20 less dependent on yielding of the paraffin 20. The smaller radii of corner curvature permitted by the molds 14, 104 may also make post-microtome handling of the embedded tissue specimens easier because the surrounding hardened paraffin 170 (see FIG. 9) is more rectangular and has more square corners than conventional approaches.

Figure 7B:
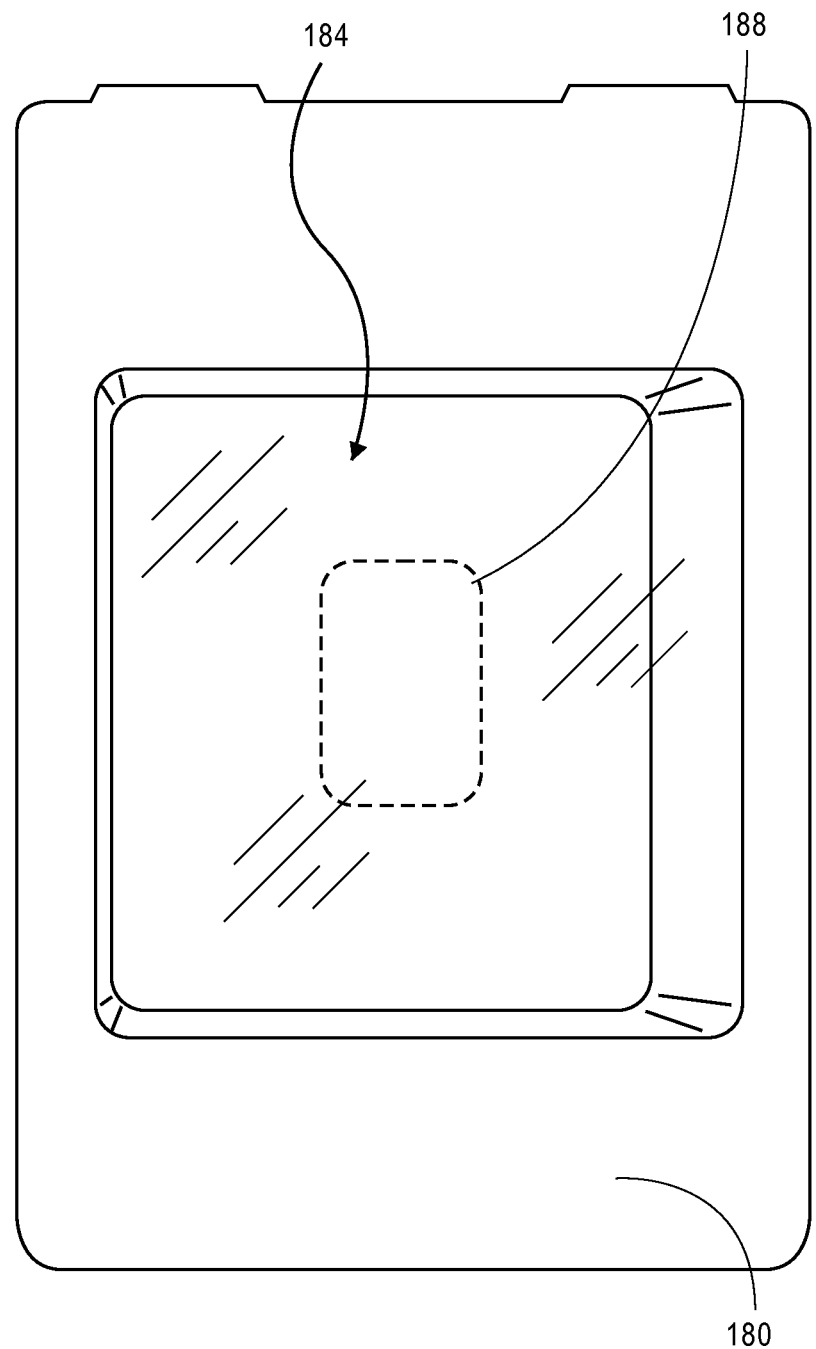
FIG. 7B is a top generally plan view of an embedded tissue specimen and cassette construct similar to FIG. 7A formed using a mold having a barrier coating.
Figure 7C:
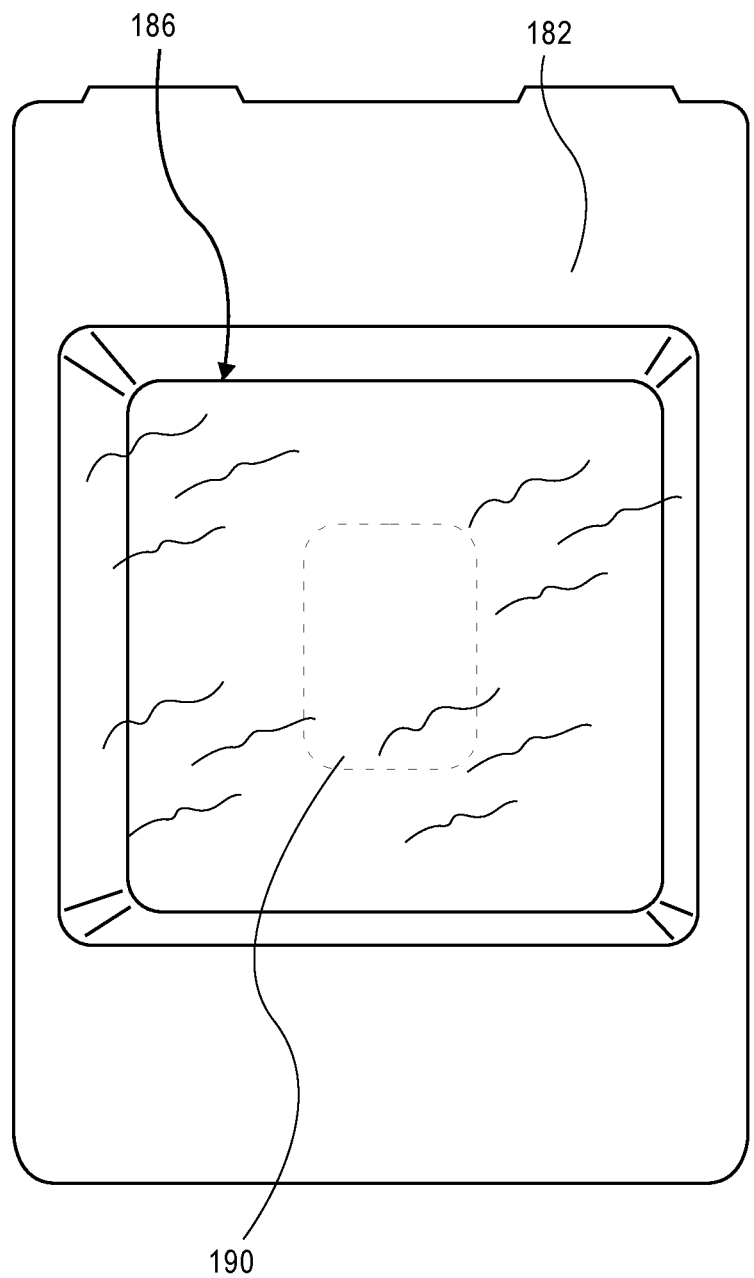
FIG. 7C is a top generally plan view of an embedded tissue specimen and cassette construct similar to FIG. 7B but formed using a traditional mold, the construct of FIG. 7C having a rougher outer surface and being less translucent than the construct of FIG. 7B.

Another benefit of the molds 14, 104 is that the barrier coating 40 resists adhesion of the paraffin 20 to the molds 14, 104. This reduction in adhesion produces a smaller crystalline structure of the hardened paraffin 20 so that the outer surfaces have a smooth, glass like texture and are more translucent than outer surfaces of paraffin 20 produced using traditional molds. For example and with reference to FIGS. 7B and 7C, two hardened paraffin samples 180, 182 are shown. The hardened sample 180 was formed using a mold having a barrier coating according to the disclosure herein whereas the hardened sample 182 was formed using a traditional mold. As shown in FIG. 7B, the hardened sample 180 has outer surfaces 184 with a smoother texture than outer surfaces 186 of the hardened sample 182. Further, because the outer surfaces 184 have fewer imperfections the outer surfaces 184 are more translucent than the outer surfaces 186. The increased translucency of outer surfaces 184 permit features of an embedded object 188, such as a tissue sample, to be more clearly visually observed than an embedded object 190 in the hardened sample 182. This is of benefit in visually determining the completeness of the embedding material infiltration into the tissue sample as well as visually determining the tissue specimen size and shape that will be presented to the cutting edge of the microtome machine 145 (see FIG. 9).

Figure 10:
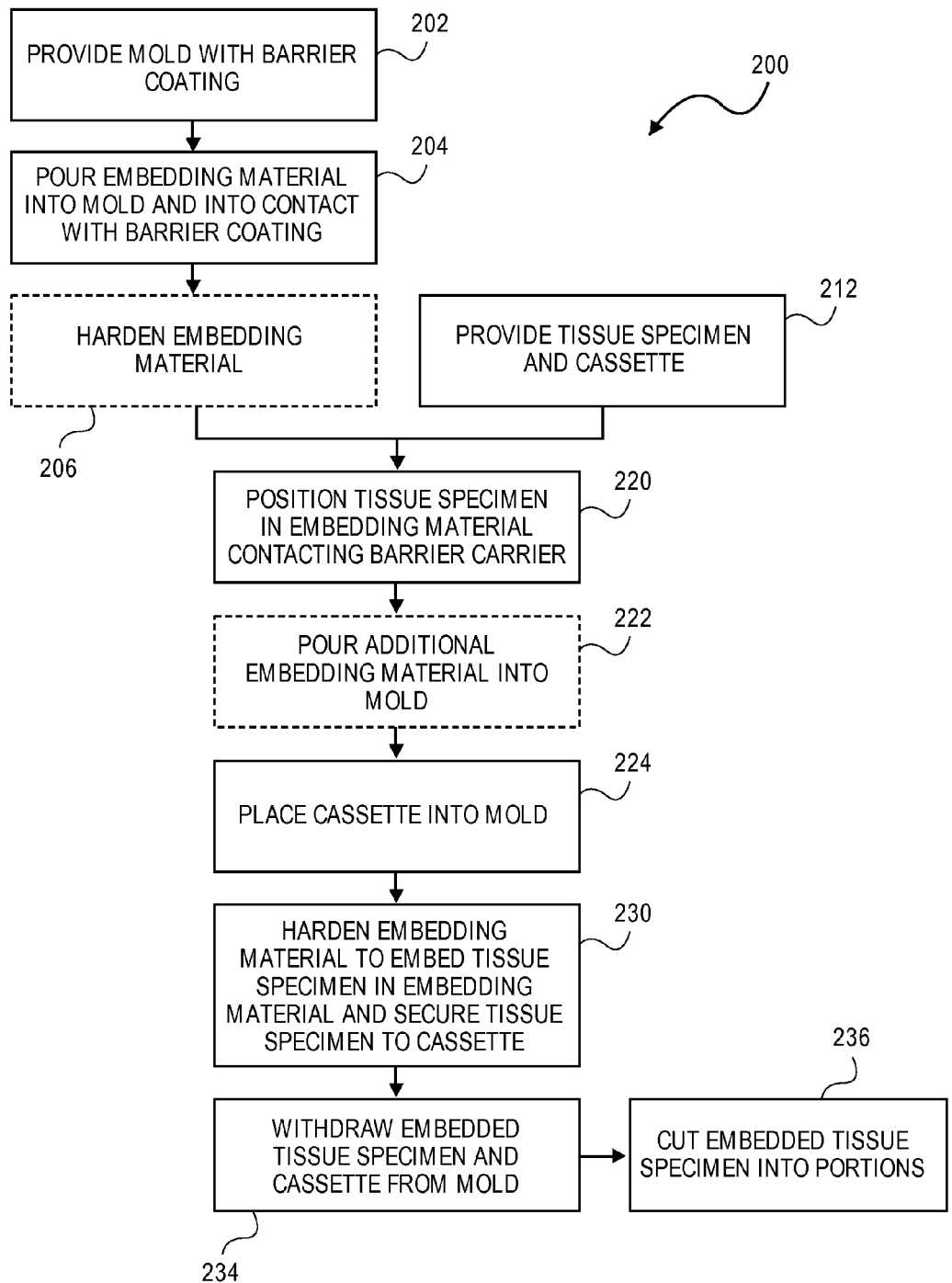
FIG. 10 is a flowchart of a method for preparing tissue specimens for histological examination.

With reference to FIG. 10, a method 200 of preparing a tissue specimen for histological examination is provided with reference to the device 10 of FIGS. 1-4. The method 200 begins with providing the mold 14 with the coating 40 (block 202). The mold 14 with the coating 40 may be manufactured off-site and shipped to a laboratory so that the mold 14 is simply removed from storage and used in the method 200.

Molten embedding material, such as paraffin wax 20, is poured into the mold 14 and into contact with the coating 40 bonded to the interior portion 42 of the mold 14 (block 204). In one approach, pouring involves filling only a portion of the cavity 16, such as a quarter or an eighth of its volume, in order to position a section of the wax 20 between the tissue specimen 22 and an interior surface of the mold bottom wall 32 (see FIG. 2D). The paraffin 20 can be poured from a beaker or dispenser reservoir and into the cavity 16 by a lab technician. In another approach, a dispensing device can be used to dispense a metered amount of molten paraffin 20 into the mold 14.

The paraffin 20 that has been poured into the mold 14 is optionally hardened (block 206). The hardening can be accomplished by simply waiting for the paraffin wax 20 to cool to ambient temperature. Alternatively, another mechanism such as a cooling rail or plate disposed below the mold bottom wall 32 can be used to cool the paraffin 20.

The method 200 further includes providing the tissue specimen 22 and the cassette 12 (block 212). Providing the tissue specimen 22 may involve treating the tissue with one or more fluids including ethanol, xylene, formaldehyde and water in order to prepare the tissue specimen 20 for further processing. The cassette 12 provided is preferably selected to cooperate with the mold 14 and be suitable for use in handling the tissue specimen 22.

Next, the tissue specimen 22 is positioned in the paraffin 20 within the mold cavity 16 (block 220). Positioning the tissue specimen 22 includes advancing the tissue specimen 22 into the cavity 16 and onto the paraffin 20 previously poured in block 204. If the paraffin 20 has cooled and partially hardened, the surface tension of the paraffin 20 will accept and capture the weight of the tissue specimen 22. In one approach, the tissue specimen 22 may be positioned manually, e.g., by using forceps, or have been positioned within unique cassettes associated with an automated mechanism.

An amount of paraffin 20 is poured into the mold 14 over the tissue specimen 22, such as from a beaker or dispenser reservoir (block 222). As discussed above, the barrier coating 40 of the mold 14 re-directs capillary forces within the paraffin 20 back into the paraffin 20 and produces an outwardly crowning, positive meniscus 21 of the paraffin 20 (see FIG. 2A). The amount of paraffin 20 poured at block 222 is preferably an amount sufficient to position the raised portion 23 of the paraffin 20 at a height within the mold 14 where the raised portion 23 will fill the perforations 25 in the cassette 12 when the cassette 12 is introduced into the mold 14. Thus, a single pour at block 222 of paraffin 20 may be sufficient to provide enough material of the paraffin 20 to weld the paraffin 20 (and the specimen 22 therein) to the cassette 12, rather than needing to subsequently pour additional paraffin 20 over the cassette 12 as in traditional approaches.

In an alternative approach, a sufficient amount of paraffin 20 is poured into the mold cavity 16 at step 204 to produce an outwardly crowning positive meniscus 21. The tissue specimen 22 is positioned 220 by advancing the specimen 22 through the paraffin 20 and onto a portion of the paraffin 20 near the cavity bottom wall 32, which has been hardened at block 206. The cassette 12 is then placed into the mold 14 and into contact with the paraffin 20 (block 224).

In block 224, the cassette 12 is placed into the mold 14 such that the cassette 12 contacts the paraffin 20. The outwardly crowning, raised portion 23 of the paraffin 20 fills the cassette perforations 25 and begins to weld the paraffin 20 to the cassette 12. In one embodiment, meniscus 21 has a sufficient volume to initiate a lateral flow of paraffin when mated with a floor or base of a cassette (cassette 12) that is optionally warmed to a temperature above a melting point of the paraffin. The coupled volume of the meniscus, with capillary forces between the outer floor of the warmed cassette, and the physical attraction of the openings in the cassette floor tends to direct the paraffin laterally and upward into the openings of the cassette floor. The lateral and upward force of attraction (paraffin to paraffin) is a positive action. It is believed that the meniscus volume that results from the surface energy of the oleophobic mold coating/surface provides the force into the approaching applied cassette where multiple openings of small diameter bring capillary forced upward flow to fill the void of the openings. Optionally, additional paraffin 20 may then be poured over the cassette 12 to add additional paraffin 20 and enhance the connection of the paraffin 20 to the cassette 12 once the paraffin 20 hardens.

The method 200 further includes hardening the paraffin 20 to embed the tissue specimen 22 in the paraffin 20 and secure the tissue specimen 22 to the cassette 12 (block 230). Hardening the paraffin 20 forms an embedded tissue and cassette construct (see FIG. 7A) and hardens at least a portion of the paraffin 20. It will be appreciated that hardening the paraffin 20 can encompass hardening a range of amounts of the paraffin, including a small amount of the paraffin 20, a majority of the paraffin 20, and substantially all of the paraffin 20. When less then all of the paraffin 20 is hardened, some of the central portions of the paraffin may remain molten for a short period of time, but will eventually harden in order to permit subsequent sectioning by a microtome.

Hardening the paraffin 20 may involve cooling the paraffin 20 from an elevated temperature to a lower temperature. The hardening process may be achieved, for example, by passively permitting the paraffin 20 to cool from an elevated temperature to an ambient temperature. In another approach, an active cooling operation may be performed such as placing the mold cavity bottom wall 32 on a cooling rail to cool the paraffin 22 via conduction through the bottom wall 32. When cooled, the captured paraffin within the applied cassette provides the hold fast element of attachment for the paraffin casting to the carrier cassette.

Next, the embedded tissue specimen 22 and cassette 12 are withdrawn from the mold 16 (block 234). As discussed above, the coating 40 reduces the frictional engagement of the paraffin 20 with the interior coated surfaces of the mold cavity 16 such that the embedded tissue and cassette construct can be withdrawn from the mold cavity 16 before the paraffin 20 has fully cooled and while the paraffin 20 is semi-solid. The reduced frictional engagement permits the paraffin 20, which may still be somewhat sticky, to be removed from the mold cavity 16 even though the central region of the paraffin 20 may still be molten. In this manner, the duration of time spent hardening the paraffin 20 can be reduced by approximately five percent to approximately twenty five percent over conventional approaches (where the paraffin wax is fully cooled before the embedded tissue specimen is withdrawn from the mold cavity). The reduced time spent hardening the paraffin 20 improves the rate of embedded tissue specimen production.

The embedded tissue sample 22 is then cut into sections to be mounted on glass slides and stained for subsequent histological examination (block 236). The cutting may be performed using a microtome 145, as shown in FIG. 9.

Figure 11:
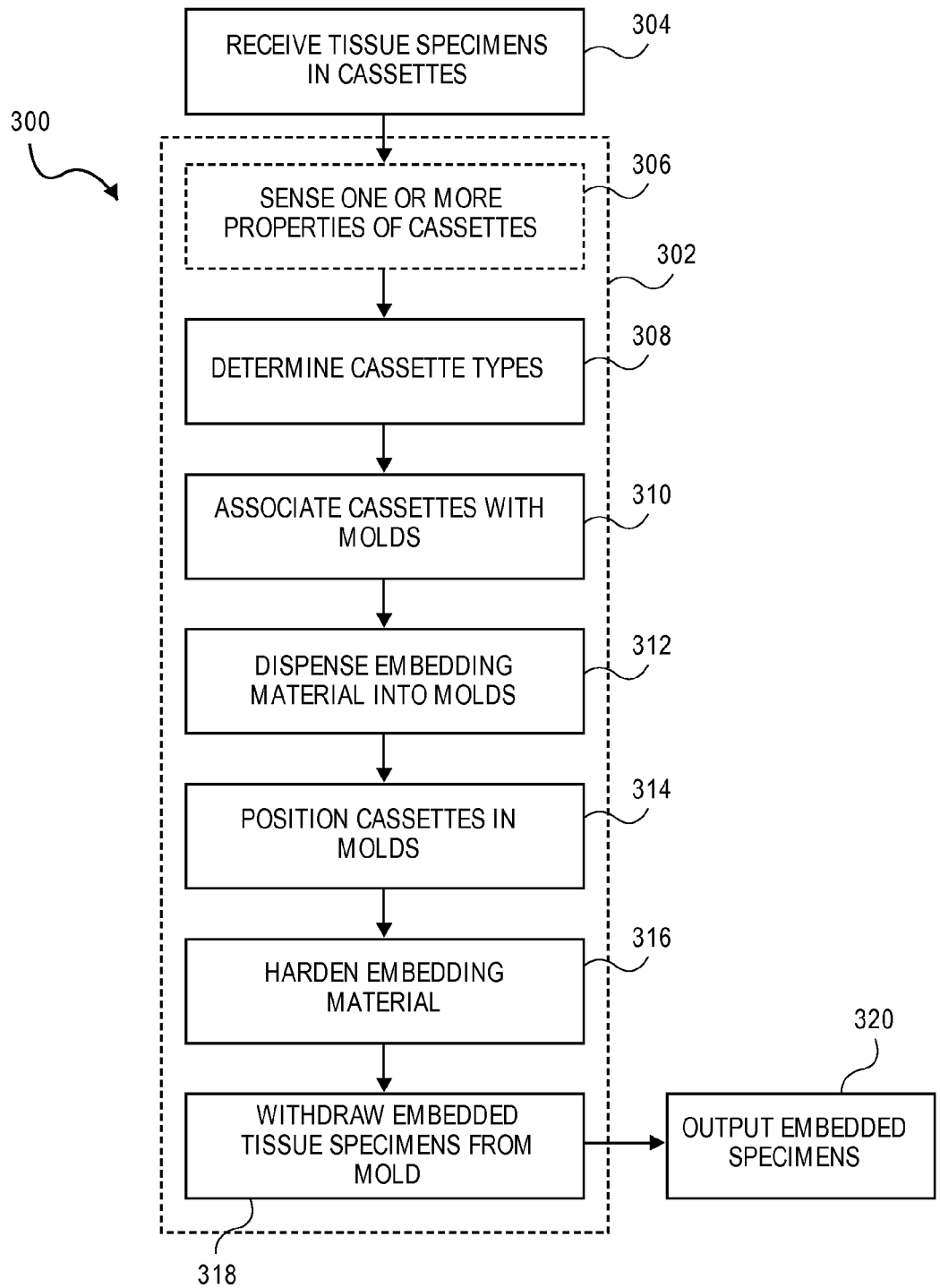
FIG. 11 is a flow chart of a method of processing tissue specimens.
Figure 12:
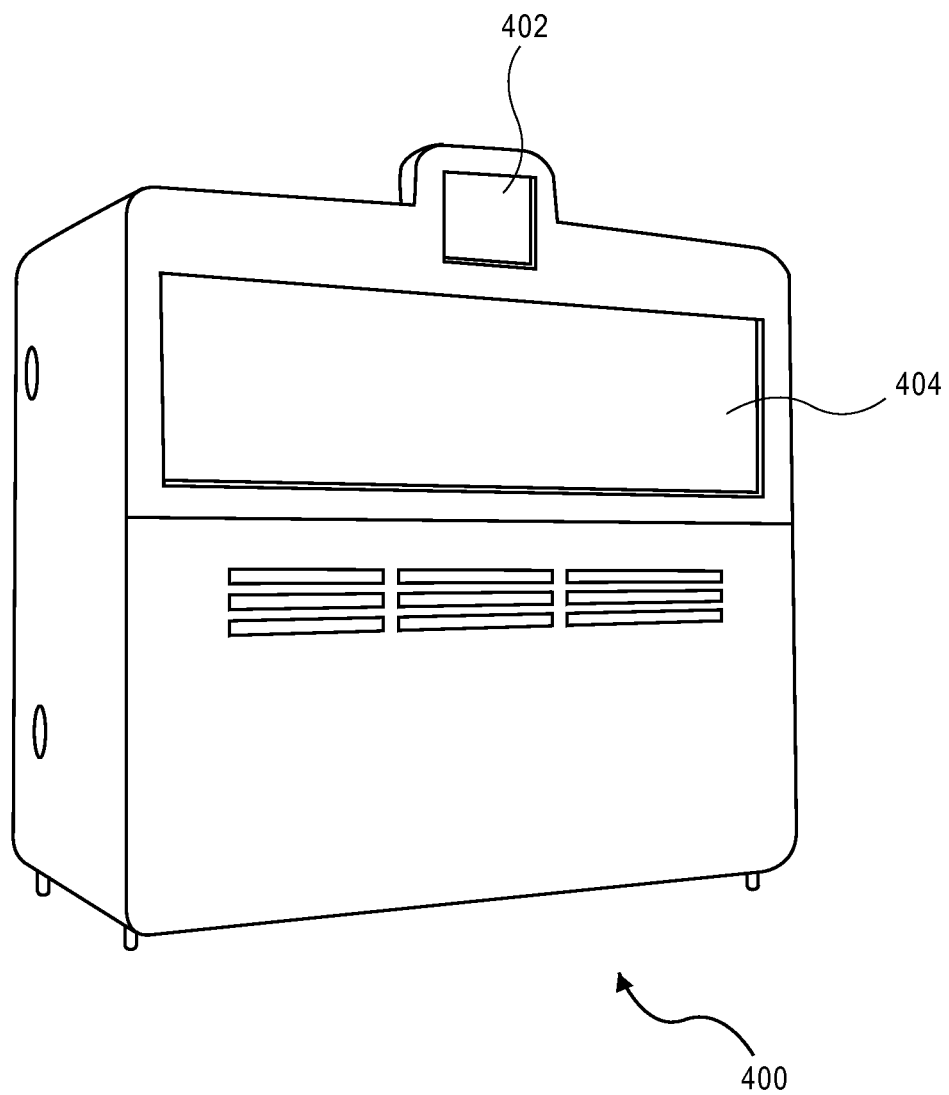
FIG. 12 is perspective view of a machine for performing at least a portion of the method of FIG. 11.

With reference to FIGS. 11 and 12, a method is provided for preparing embedded tissue specimens using an automated tissue sample processing machine 400. The method includes a portion of the method that may be performed in a substantially automated manner once the machine 400 has been appropriately configured and provided with the requisite supplies. It will be appreciated that many aspects of the method 300 are similar to processes of the method 200 such that a detailed discussion of these aspects will be omitted for brevity.

The machine 400 receives tissue samples in cassettes or capsules (block 304). There are a large variety of cassettes or capsules that have been developed for preparing tissue specimens for histological examination, and it is contemplated that a mold and cassette, such as mold 14 and cassette 12, are selected according to, for example, the size of the tissue specimen, type of tissue specimen, type of testing to be performed, and microtome to be used.

The machine 400 may optionally sense one or more properties of the cassettes (or capsules if used) (block 306). The machine can have an internal sensor 404 that is configured and arranged to sense the cassettes received by the machine 400. As one example in this regard, the cassettes could each bear an optical code (such as, but not limited to, a bar code or the like) that identifies the cassette (such as its shape, size, location of the tissue specimen received therein, etc.), and the sensor 404 can include an optical code reader that is configured and arranged to scan the cartridge's optical code. As another example, the sensor 404 could include an image capture device, such as a digital camera, that operates with machine 400 hardware and software to identify the cassettes being received by the machine 400. As an alternative approach, a user enters information into a user interface 402 (see FIG. 11) that relates to one or more properties of the cassettes being loaded into the machine 400. The machine could also be connected to a network and receives information regarding the cassettes from a remote computer, such as a workstation.

Whether the one or more properties have been determined using the machine sensor 404, information obtained from user interface 402, a combination of both, or another approach, the method 300 further includes determining the types of cassettes received by the machine 400 (block 308).

Next, the cassettes are associated with molds that correspond to the cassettes based at least in part on determining the types of cassettes present in the machine 400 (block 310). The molds have barrier coatings, such as coating 40, intimately bonded with one or more surfaces of the molds. The barrier coatings may be different for different types of molds and their associated cassettes. The molds may be stored within the machine 400 or, as another example, may be loaded into the machine 400 contemporaneously with the cassettes.

The machine 400 then dispenses embedding material, such as paraffin wax 20, into the molds (block 312). The amount of embedding material dispensed may be based in part on the cassette types determined and the molds associated with the cassettes.

The machine 400 positions the cassettes in the associated molds, and the embedding material is hardened (block 314 and block 316). The molds have barrier coatings, such as coating 40 discussed above, which reduce coefficient of friction between the embedding material and the molds. Hardening the embedding material therefore can encompass hardening less than all of the embedding material for each mold, as discussed above with respect to method 200.

The method 300 includes withdrawing the embedded tissue samples from the molds (block 318). Withdrawing the embedded tissue samples can include removing the embedded tissue samples before the embedding material has completely hardened. For example, the tissue samples embedded within paraffin wax can be removed while a central portion of the paraffin is still semi-molten and soft. The barrier coatings of the molds permit this accelerated withdrawal of the embedded tissue specimen because of the decreased frictional engagement between the embedding material and the molds. This decrease in time spent hardening the embedding material can increase the throughput of the machine 400 by reducing the time spent hardening the embedded tissue specimens within the molds.

Finally, the method 300 includes outputting the embedded tissue specimens (block 320). In one form, the embedded tissue specimens could be outputted from machine 400 and then withdrawn from the molds. The embedded tissue specimen may then be transferred to a microtome machine for sectioning.

EXAMPLES

The following examples pertain to embodiments:

Example 1 is a tissue embedding mold including a bottom wall and sidewalls defining an interior volume and a paraffin resistant material coating on a portion of the bottom wall and sidewalls.

In Example 2, the paraffin resistant material of Example 1 includes an oleophobic material.

In Example 3, the sidewalls of Example 1 include primary sidewalls and the bottom wall including a primary bottom wall and includes a cavity including secondary sidewalls and a secondary bottom wall defining a plane different than a plane of the primary bottom wall.

In Example 4, the secondary sidewalls of Example 3 extend at a draft angle of 0 degrees to 2 degrees relative to a perpendicular projection from the secondary bottom wall.

In Example 5, the paraffin resistant material of Example 3 is coated on the secondary sidewalls and the secondary bottom wall.

Example 6 is a method including introducing an embedding material into a mold including a bottom wall and sidewalls defining an interior volume, wherein the mold includes a paraffin resistant material coating on a portion of the bottom wall and sidewalls; and inserting a tissue sample into the embedding material.

In Example 7, the method of Example 6 further includes inserting a cassette into the embedding material.

In Example 8, the inserting of a cassette in Example 7 follows the inserting the tissue sample, and the introducing of the embedding material includes introducing an amount of embedding material such that the cassette is welded to the embedding material without the need for introduction of additional embedding material.

In Example 9, the embedding material of Example 8 has a property to harden to a solid following introduction into the mold.

In Example 10, the method of Example 6 further includes removing the embedding material from the mold.

In Example 11, the embedding material of Example 10 has a property to harden to a solid following introduction into the mold and the method includes removing the embedding material from the mold prior to hardening to a solid.

Example 12 is a method of making a tissue embedding mold including coating a portion of a bottom wall and sidewalls defining an interior volume with a paraffin resistant material.

In Example 13, the sidewalls of Example 12 include primary sidewalls and the bottom wall includes a primary bottom wall and comprises a cavity including secondary sidewalls and a secondary bottom wall defining a plane different than a plane of the primary bottom wall.

In Example 14, the secondary sidewalls of Example 13 extend at a draft angle of 0 degrees to 2 degrees relative to a perpendicular projection from the secondary bottom wall.

In Example 15, the paraffin resistant material of Example 13 is coated on the secondary sidewalls and the secondary bottom wall.

In Example 16, the paraffin resistant material of Example 12 includes an oleophobic material.

While there have been illustrated and described particular embodiments of the present invention, it will be appreciated that numerous changes and modifications will occur to those skilled in the art, and it is intended that all those changes and modifications fall within the true spirit and scope of the present invention. For example, although the methods detailed above are described using a cassette, the methods can be used with capsules or other devices for containing or supporting tissue specimens. As another example, the method operations discussed above can be re-ordered, combined, eliminated, and modified as desired for a particular application.

What is claimed is:

1. A tissue embedding mold comprising a bottom wall and sidewalls defining an interior volume and a paraffin resistant material coating on the entire bottom wall and sidewalls, wherein the sidewalls are oriented at a draft angle relative to the bottom wall and the draft angle is in a range of zero degrees to two degrees, wherein the tissue embedding mold comprises dimensions operable for loading into a tissue sample processing machine, wherein the paraffin resistant material comprises a self-assembled monolayer of phosphates.

2. The tissue embedding mold of claim 1, wherein the paraffin resistant material comprises an oleophobic material.

3. The tissue embedding mold of claim 1, wherein the sidewalls comprise primary sidewalls and the bottom wall comprises a primary bottom wall and comprises a cavity including secondary sidewalls and a secondary bottom wall defining a plane different than a plane of the primary bottom wall.

4. The tissue embedding mold of claim 3, wherein the secondary sidewalls extend at a draft angle of 0 degrees to 2 degrees relative to a perpendicular projection from the secondary bottom wall.

5. The tissue embedding mold of claim 3, wherein the paraffin resistant material is coated on the secondary sidewalls and the secondary bottom wall.

6. The tissue embedding mold of claim 1, wherein the paraffin resistant material comprises a glaze.

7. The tissue embedding mold of claim 1, wherein the mold comprises stainless steel.

* * * * *